(12) United States Patent
Gilbard et al.

(10) Patent No.: US 8,535,736 B2
(45) Date of Patent: Sep. 17, 2013

(54) METHODS AND COMPOSITIONS FOR THE TREATMENT OF INFECTION OR INFECTIOUS COLONIZATION OF THE EYELID, OCULAR SURFACE, SKIN OR EAR

(75) Inventors: Jeffrey P. Gilbard, Weston, MA (US); Elisabeth Gilbard, Weston, MA (US)

(73) Assignee: Advanced Vision Research, Inc, Woburn, MA (US)

( * ) Notice: Subject to any disclaimer, the term of this patent is extended or adjusted under 35 U.S.C. 154(b) by 0 days.

(21) Appl. No.: 13/523,512

(22) Filed: Jun. 14, 2012

(65) Prior Publication Data

US 2012/0270953 A1    Oct. 25, 2012

Related U.S. Application Data

(60) Continuation of application No. 12/854,272, filed on Aug. 11, 2010, now abandoned, which is a division of application No. 11/404,335, filed on Apr. 13, 2006, now abandoned.

(51) Int. Cl.
*A01N 65/00* (2009.01)

(52) U.S. Cl.
USPC ........................................ 424/725

(58) Field of Classification Search
None
See application file for complete search history.

(56) References Cited

U.S. PATENT DOCUMENTS

| | | | |
|---|---|---|---|
| 4,261,904 | A | 4/1981 | Takeda et al. |
| 5,009,890 | A | 4/1991 | Dipippo |
| 5,384,125 | A | 1/1995 | Dipippo |
| 6,585,961 | B1 | 7/2003 | Stockel |
| 7,485,327 | B2 | 2/2009 | Kim et al. |
| 2002/0173436 | A1 | 11/2002 | Sonnenberg et al. |
| 2003/0157138 | A1 | 8/2003 | Eini et al. |
| 2003/0161867 | A1 | 8/2003 | Lu et al. |
| 2005/0158405 | A1 | 7/2005 | Boukas |
| 2005/0220742 | A1 | 10/2005 | van Breen |
| 2006/0057075 | A1 | 3/2006 | Arkin et al. |
| 2006/0068044 | A1 | 3/2006 | Reynolds |
| 2006/0275218 | A1 | 12/2006 | Tamarkin et al. |
| 2007/0003508 | A1 | 1/2007 | Wooley et al. |
| 2007/0243275 | A1 | 10/2007 | Gilbard |
| 2008/0241201 | A1 | 10/2008 | Warr et al. |
| 2010/0324151 | A1 | 12/2010 | Gilbard |

FOREIGN PATENT DOCUMENTS

| | | |
|---|---|---|
| EP | 0950399 A2 | 10/1999 |
| FR | 2866564 A1 | 8/2005 |
| JP | 2002-037747 A | 2/2002 |
| RU | 2085204 C1 | 7/1997 |
| WO | 01-70215 A1 | 9/2001 |
| WO | 2006-119174 A1 | 11/2006 |
| WO | 2007-120817 A2 | 10/2007 |

OTHER PUBLICATIONS

Brand et al., Tea tree oil reduces histamine-induces oedema in murine ears, Inflammation Research: Official Journal of the European Histamine Research Society, Jun. 2002, vol. 51., No. 6, p. 283-289 (XP002688582).
European Search Report for EP 07 755402, issued Dec. 5, 2012, 3 pages.
Faran et al., Tea tree oil: in vitro efficacy in otitis externa, The Journal of Laryngology and Otology, Mar. 2005, vol. 119, No. 3, p. 198-201 (XP9165425).
International Search Report for PCT/US2010/033140, mailed Jun. 18, 2010, 3 pgs.
Naithani, et al., *Ocimum gratissimum, Ocimum canum* and *Ocimum kilimandscharicum*: a review, Journal of Medical and Aromatic Plant Sciences, 2002, vol. 24, p. 441-455.
Wikipedia, "Linalool", 3 pages, 2008.
Ezine articles, 2009, 4 pages.
Kheirkhah, et al., Corneal manifestations of ocular demodex infestation, American Journal of Opthalmology, May 2007, 743-749.
Patent Cooperation Treaty, International Search Report for PCT/US2007/009119, mailed Jan. 7, 2008, 1 page.

*Primary Examiner* — Michael Meller
(74) *Attorney, Agent, or Firm* — Bryan Cave LLP

(57) ABSTRACT

The instant invention provides methods and compositions for the treatment of infection or infectious colonization of the eyelid and/or ocular surface for the treatment and prevention of ocular disorders and eyelid disorders.

13 Claims, No Drawings

METHODS AND COMPOSITIONS FOR THE TREATMENT OF INFECTION OR INFECTIOUS COLONIZATION OF THE EYELID, OCULAR SURFACE, SKIN OR EAR

RELATED APPLICATIONS

This patent application claims priority under 35 U.S.C. section 120 as a continuation of Ser. No. 12/854,282, currently pending, entitled "METHODS AND COMPOSITIONS FOR THE TREATMENT OF INFECTION OR INFECTIOUS COLONIZATION OF THE EYELID, OCULAR SURFACE, SKIN OR EAR" filed on Aug. 11, 2010, which is a divisional of U.S. patent application Ser. No. 11/404,335, currently pending, entitled "METHODS AND COMPOSITIONS FOR THE TREATMENT OF INFECTION OR INFECTIOUS COLONIZATION OF THE EYELID, OCULAR SURFACE, SKIN OR EAR" and filed on Apr. 13, 2006, which is hereby incorporated by reference in its entirety.

BACKGROUND OF THE INVENTION

Bacterial colonization of the eyelids is normal, but there are a number of conditions where this bacterial colonization or bacterial over-colonization of the eyelids poses a problem. One of the most serious complications of eye surgery is a secondary infection of the eyeball called endophthalmitis. It has been shown that the bacteria that cause endophthalmitis come from the eyelid margin (Speaker M G, Milch F A, Shah M K, et al. Role of external bacterial flora in the pathogenesis of acute postoperative endophthalmitis. Ophthalmology (United States), May 1991, 98(5) p 639-49). Another condition of clinical significance is inflammation of the eyelids that frequently results in symptoms of eye irritation called blepharitis. In a study involving 332 patients with blepharitis and 160 normal controls, it has been shown that blepharitis patients have greater quantities of bacteria on their eyelids compared to normal controls. This finding applied to patients with both anterior and posterior blepharitis (Groden L R, Murphy B, Rodnite J, et al. Lid flora in blepharitis. Cornea (United States), January 1991, 10(1) p 50-3). Bacterial overgrowth has been hypothesized to contribute to the symptoms of blepharitis by the production of bacterial lipases and esterases that hydrolyze the wax and sterol esters in meibum, creating free fatty acids that are irritating to ocular tissue and may effect tear film stability (Ta C N, Shine W E, McCulley J P, et al. Effects of minocycline on the ocular flora of patients with acne rosacea or seborrheic blepharitis. Cornea (United States), August 2003, 22(6) p 545-8). In addition these fatty acids may promote eyelid and ocular surface inflammation (Shine W E, McCulley J P, Pandya A G Minocycline effect on meibomian gland lipids in meibomianitis patients. Exp Eye Res (England), April 2003, 76(4) p 417-20).

Moreover, a condition known as dry eye causes chronic eye irritation resulting from decreased tear production or increased evaporation that results in a loss of water from the tear film and an increase in tear film osmolarity. This increase in tear film osmolarity results in an osmotic dehydration of the surface associated with a decrease in the density of conjunctival goblet cells. Recently it has been shown that dry eye patients have increased bacterial colonization of their eyelids, and that the bacteria found in these patients decrease the proliferation of conjunctival goblet cells in tissue culture ((Graham et al Analysis of Bacterial Flora in Dry Eye, Ocular Surface, 3(1):S68, 2005).

Punctal plugs are a frequently used treatment for dry eye. They provide symptomatic relief for patients with dry eye, reduce elevated tear film osmolarity in the disease and reduce ocular surface staining. A problem with punctal plugs is that they are frequently colonized by pathogenic noncomensals, including *Pseudomonas aeruginosa* and *Staphylococcus aureus*, that may cause symptoms and increase the risk of eye infections (Soukiasian S H Microbiology of Explanted Punctal Plugs, ARVO Annual Meeting, Program#/Poster#4981/B305, Apr. 29, 2004).

Eyelid or lid hygiene has been recommended for all of these conditions or circumstances by eye doctors. The most common recommendation is to dilute baby shampoo 1:10 with water, and to use the dilution to moisten a pad or cotton tip swab to scrub the lid margin. In addition there are multiple products on the market that package gentle soap with pads or cotton tips or saturate pads with such soap, to facilitate performing eyelid hygiene or cleansing. None of these products is sufficiently anti-bacterial to kill eyelid bacteria within clinically relevant exposure times.

Accordingly, a need exists for an effective antibacterial preparation that can be used in or around the eye and does not cause clinically significant conditions to the site of application.

SUMMARY OF THE INVENTION

There are multiple antibacterial soaps and cleansers on the market. The active agents in these products included Triclocarban, Triclosan, Benzalkonium Chloride, ethyl alcohol, alkyl dimethyl benzyl, and ammonium chloride. All of these antibacterial preparations are toxic and can not be used on the eyelids or around the eye. Moreover, these antibacterial soaps and cleansers bear labels warning about eye contact.

Tea tree oil has been recognized for some time as having antibacterial activity, with the activity being bactericidal at high concentrations and bacteriostatic at lower concentrations. For the most part, studies on tea tree oil have looked at the minimal inhibitory concentrations and minimal bactericidal concentrations. Clinical resistance to tea tree oil has not been reported. Research has examined various components of tea tree oil in order to determine which contribute to its antibacterial effect. Two of these components are linalool and alpha-terpineol, both of which have been considered to have antibacterial activity similar to or less than tea tree oil itself (Carson C F, Hammer K A, Riley T V Melaleuca alternifolia (Tea Tree) Oil: a Review of Antimicrobial and Other Medicinal Properties Clin Microbiol Rev (United States), January 2006, 19(1) p 50-62).

In fact, using disc diffusion and broth dilution methods, linalool and alpha-terpineol were found to be inactive against *P. aeruginosa*, just as whole tea tree oil, using disc diffusion, had been shown to be inactive against *Pseudomonas*. The major antibacterial activity of tea tree oil has been principally attributed to terpinen-4-ol (Southwell I. A., Hayes A. J., Markham J. and Leach D. N. The search for optimally bioactive Australian tea tree oil. Acta Horticulturae (1993) 334, 256-265; Carson C F, Riley T V Antimicrobial activity of the major components of the essential oil of Melaleuca alternifolia. J Appl Bacteriol (England), March 1995, 78(3) p 264-9). In kill-time studies, tea tree oil, at a concentration of 0.50%, has been shown to require 30 minutes to produce an approximately 1 log reduction in *S. aureus* (Cox S D, Mann C M, Markham J L, et al. The mode of antimicrobial action of the essential oil of Melaleuca alternifolia (tea tree oil). J Appl Microbiol (England), January 2000, 88(1) p 170-5). In a separate study, 1.0% tea tree oil required 15 minutes to produce a 1.3 log reduction in *S. aureus*, while 2.0% tea tree oil required 5 minutes to produce a 1.4 log reduction in *S. aureus* (Christoph R, Stahl-Biskup E. Death kinetics of *Staphylococcus aureus* exposed to commercial tea tree oils J Essent Oil Res, March/April 2001, 13:98-102). These concentrations of tea tree oil are irritating to the eye and require too long of a contact time to be clinically useful in killing bacteria on the eyelid margin, or for use on the skin.

Accordingly, the instant invention provides compositions for the treatment of infection or infectious colonization that contain amounts of linalool and/or α-terpineol oil, that are effective in clinically acceptable time frames, and do not cause clinically significant conditions to the site of application. The compositions may further contain tea tree oil.

Specifically, the invention provides a topical preparation containing linalool oil, and a membrane permeablizer, wherein the linalool is present in a quantity that is bactericidal against gram negative bacteria and gram positive bacteria but does not cause clinically significant conditions to the site of application. The preparation may also contain water. The preparation may also contain a pharmaceutically acceptable carrier.

Additionally, the invention provides a topical preparation that has α-terpineol oil, and a membrane permeablizer, wherein the α-terpineol is present in a quantity that is bactericidal against gram negative bacteria and gram positive bacteria but does not cause clinically significant conditions to the site of application. The preparation may also contain water. The preparation may also contain a pharmaceutically acceptable carrier.

The topical preparation may further contain an emulsifier, e.g., a surfactant.

Specific preparations contain linalool in a final concentration of at least about 0.7%, between about 0.7% and about 1.5%, between about 0.80% and about 1.25% or about 0.90%.

The topical preparation may further contain tea tree oil. The tea tree oil may be present in a final concentration of between about 0.0125% and about 0.050%, about 0.02% and about 0.04%, or about 0.025%.

The membrane permeabilizer can be a polycationic substance, a cationic detergent or a chelator. In one formulation, the membrane permeablizer is Tris-EDTA and is present in a concentration of about 0.01% to about 0.06%. Specifically, the Tris-EDTA is present in a concentration of about 0.03%.

One exemplary topical preparation has about 0.90% linalool and 0.03% Tris-EDTA.

The topical preparations of the invention may result in at least about a 1 log reduction in colony-forming units of *Staphylococcus aureus*, methicillin-resistant *Staphylococcus aureus, Serratia marcescens* or *P. aeruginosa* after 1 minute of exposure to the topical preparation.

The invention also provides methods using the topical preparations of the invention. Specifically, the invention provides methods of cleaning an eyelid of a subject, methods of treating an ocular disorder in a subject, e.g., an ocular disorder such as blepharitis, dry eye, and hordeolums, methods of treating an infection of the ocular surface in a subject, e.g., an infection such as conjunctivitis or corneal ulcer, methods of preventing an infection of the eye in an eye surgery patient, e.g. a cataract or LASIK eye surgery patient, a method of disinfecting punctal plugs in a patient wearing punctal plugs, and methods of treating an ear or skin infection in a subject. The methods entail applying the topical preparation to the area that is infected, or at risk of being infected, or is the source of bacteria for an infection, thereby treating or preventing an infection in the subject. According to the methods of the invention, the topical preparations can be applied as necessary to treat or prevent an infection.

The invention provides kits that contain a topical preparation of the invention and instructions for use. The kits may further contain an applicator.

DETAILED DESCRIPTION OF THE INVENTION

At present, there exists a need for compositions and methods for treating or preventing an infection of the eye or surrounding area. In certain embodiments, the compositions are also useful for treating or preventing infection of the ear or skin.

DEFINITIONS

The invention will be described with reference to following definitions that, for convenience, are collected here.

The term "cleaning an eyelid" is used herein to describe the act of significantly reducing the amount of dirt, debris, or bacteria, from an eyelid.

The term "dry eye" is known in the art as a condition of a subject that has a loss of water from the tear film. Dry eye is often an age related disease. Posterior blepharitis or meibomitis is associated with inflammation of the tarsal and bulbar conjunctiva, and complicated by hordeolums and chalazions, and leads to meibomian gland dysfunction. Meibomian gland dysfunction is a common cause of dry eye and manifests itself in such forms as stenosis or closure of the meibomian gland orifices. Meibomian gland dysfunction is commonly linked with ocular rosacea, blepharitis, and other inflammation of the eyelids. Both anterior and posterior blepharitis are associated with bacterial overcolonization of the eyelids.

The term "eyelid" as used herein, includes the tarsal conjunctival surface, both the interior and exterior surfaces of the eyelid, the eyelid margin, the glands in and around the eyelid margins, the hair follicles of the eyelid, the eyelashes, and the periocular skin surrounding the eye.

The term "eyelid disorder" is defined as a disorder that results in inflammation of the eyelashes and/or eyelash follicles and/or eyelid margins, or inflammation of the lipid producing glands that are located in the eyelid. Exemplary eyelid disorders include, but are not limited those caused by bacterial infection.

The term "ocular disorder" as used herein, includes ocular surface disorders, disorders of the eyeball, periocular skin disorders, and eyelid disorders. Exemplary ocular disorders include, but are not limited to dysfunctions of the tear film, inflammation of the eyelid margins due to bacterial infection, infections inside the eye known as endophthalmitis, and dry eye.

The term "treatment" as used herein is defined as prophylactic treatment (e.g., daily preventative use) or therapeutic treatment (e.g., a single treatment or a course of treatment) of a subject with or at risk for an ocular disorder, or with an ear or skin infection, which results in the reduction, alleviation, or elimination of infectious or bacterial colonization of the treated area.

The term "topical preparation" as used herein includes antibacterial compositions comprising a membrane permeablizer and an antibacterial composition, e.g., linalool oil or α-terpineol oil. The topical preparations of the invention can be a cream, liquid, paste, solution, ointment, gel or the like. The topical preparations of the invention can be applied to the skin, eye, eyelid, ear canal or ear.

The term "clinically significant conditions" is intended to mean conditions, disorders, and side effects associated with the application of the topical preparations of the invention. The term is intended to include irritation, toxicity, cell damage, and the like that is caused by the application of the topical preparations of the invention. In a specific example, the clinically significant condition is irritation of the eye, eyelid, or eyelid margin. Clinically significant conditions are those whose severity outweighs the therapeutic or preventative effects of the topical preparations disclosed herein as determined by one of skill in the art, i.e., a physician. The ordinary skilled artisan would be able to determine whether the conditions caused by the topical preparations disclosed herein are clinically significant.

The resistance of certain gram negative bacteria, e.g., *P. aeruginosa*, to tea tree oil, or the antibacterial components of tea tree oil, has been attributed to the outer membrane of these bacteria. It is well known that a wide range of polycationic substances and chelators can act as permeabilizers of the lipopolysaccharide outer cell membrane. Accordingly, the instant invention provides topical preparations comprising membrane permeabilizers and one or more bacteriostatic or bactericidal compositions. The topical preparations of the invention are effective against both gram-negative and gram positive bacteria, but do not cause clinically significant conditions at the site of application.

Methods and Compositions

Maintaining the health and cleanliness of the eyelid and surrounding tissue is a critical step in treating and preventing a number of ocular disorders. Effective health and cleanliness of an eye is dependant upon the ability to control the level of gram positive and gram negative bacteria. Likewise, the ability to reduce the level of bacteria is also beneficial for the treatment or prevention of other infections, e.g., eyeball, ear or skin infections.

The present invention provides compositions and methods, which decrease, e.g., significantly decrease, the number of bacteria present in or around, for example, an eye.

Accordingly, the invention is directed to a topical preparation comprising an antibacterial oil naturally found in tea tree oil, i.e., linalool oil or α-terpineol oil, and a membrane permeabilizer. The topical preparation may also contain a pharmaceutically acceptable carrier or water. The preparation may be specifically formulated for the treatment of a particular disorder, e.g., an ocular disorder selected from blepharitis, dry eye, infectious conjunctivitis, or an ear infection, or a skin infection. Accordingly, one of skill in the art would understand that the topical preparation of the invention may be in the prepared in the form of drops, solution, paste, cream, foam, gel, ointment, or the like.

Toxicity is an issue with any formulation to be used in or near the eye. The toxicity of tea tree oil has been studied and is observed at concentrations of 0.03% and higher (Soderberg T A, Johansson A, Gref R Toxic effects of some conifer resin acids and tea tree oil on human epithelial and fibroblast cells. Toxicology (Ireland), Feb. 22 1996, 107(2) p 99-109). Higher concentrations often lead to irritation of the treated area. The topical preparations described herein are formulated such that they maintain antibacterial activity but do not cause clinically significant conditions at the site of infection.

The efficacy of the topical preparations described herein is due, at least in part, to the presence of a membrane permeablizer. Exemplary membrane permeabilizers include chelators, large polycationic substances, and cationic detergents. Specific exemplary permeabilizers include polymyxin, polymyxin nonapeptides, and other derivatives, lysine polymers and protomine, small polycationic peptides, bactericidal/permeability-increasing protein, compound 48/80, aminoglycosides, Tris, $Ca^{2+}$, $Mg^{2+}$, and $Na^+$, EDTA, Tris-EDTA, nitrilotriacetate, sodium hexametaphosphate, acetylsalicylate and ascorbate (Vaara M Microbiol Rev (United States), 1992, 56(3) p 395-411).

As used herein the language "pharmaceutically acceptable carrier" is intended to include any and all solvents, agents, and the like, compatible with pharmaceutical administration. The use of such media and agents for pharmaceutically active substances is well known in the art. Except insofar as any conventional media or agent is incompatible with the topical preparations described herein, such media can be used in the compositions of the invention. Pharmaceutical compositions suitable for topical application preferably take the form of an ointment, cream, lotion, paste, gel, spray, aerosol, or oil. Exemplary carriers which may be used include petroleum jelly, mineral oil, lanolin, polyethylene glycols, alcohols, and combinations of two or more thereof.

In certain embodiments, the topical preparation is an aqueous solution and further comprises an emulsifier. In particular embodiments, the emulsifier is a surfactant. Surfactants are generally classified according to the type and charge of the hydrophilic molecular moiety. In this connection, it is possible to use surfactants classified in any one of the following groups in the compositions of the invention: anionic surfactants, cationic surfactants, amphoteric surfactants and non-ionic surfactants.

In one embodiment, the topical preparations of the invention include linalool oil. In specific embodiments, the topical preparation comprises at least about 0.7% linalool oil. In other embodiments, the topical preparation comprises between about 0.7% and about 1.5% linalool oil, between about 0.8% and about 1.25% linalool oil, or between about 1.00% and about 4% linalool. One exemplified topical preparation comprises about 0.9% linalool oil.

In other embodiments, the topical preparation also includes tea tree oil. In specific embodiments, the topical preparation comprise an amount of tea tree oil that does not cause clinically significant conditions at the site of application. In certain embodiments, the topical preparation comprises between about 0.01% and about 0.050% tea tree oil, or between about 0.02% and about 0.04% tea tree oil. One exemplified topical preparation comprises about 0.025% tea tree oil.

The compositions set forth herein can be formulated to include α-terpineol oil in place of linalool oil. Topical preparations comprising α-terpineol oil typically comprise at least about 0.50% α-terpineol oil. In specific embodiments, the α-terpineol oil is present in an amount between about 0.50% and about 1.0%, or about 1.0% and about 3.0%. One exemplified topical preparation comprises about 0.75% α-terpineol oil.

In a further embodiment of the invention, the topical preparations can include both linalool and α-terpineol oil. In one embodiment, the α-terpineol oil replaces an amount of linalool that has approximately the same bactericidal efficacy.

The topical preparations may further include buffers, solubilizers, viscosity increasing agents, preservatives, anti-inflammatory agents and salts.

The invention is further directed to methods of using the compositions described above to treat a subject, e.g., a subject having or at risk of having an infection, e.g., an infection of the eye or skin. The method comprises the step of applying the topical preparation described herein to the site of the infection, or site where an infection is likely to occur, or the site from which an infection might originate, for a time and under conditions effective for reducing the amount of bacteria present. In a specific embodiment, the time and conditions selected result in an at least about 1 log reduction in colony-forming units of the infecting bacteria after one minute of exposure to the topical preparation. In other embodiments, the application of the topical preparation for one minute results in an at least about 2, 3, 4 or 5 log reduction in colony-forming units.

In specific methods, the invention provides methods of cleaning an eyelid by applying the topical preparations provided herein to the eyelid of a subject. The invention also provides methods of treating ocular disorders such as blepharitis, dry eye, infectious conjunctivitis, and other ocular disorders that result from the bacterial infection of the eye or surrounding tissue, by applying the topical preparations provided herein to the eye and/or surrounding tissue of a subject.

The invention also provides methods of treating infection of the ocular surface by applying the topical preparations provided herein to the eye of a subject. Exemplary infections that can be treated with the topical preparations provided herein include conjunctivitis, e.g., infectious conjunctivitis and corneal ulcers.

The invention also provides methods of preventing an eye infection in a subject having an eye surgery or procedure. These methods would comprise applying the topical preparation to the eye over a number of days preceding the surgery or procedure to reduce or eliminate the risk of developing an infection during the surgery or procedure. Exemplary procedures include cataract or LASIK surgery.

The invention also provides methods of maintaining low bacterial colony counts on punctal plugs that have been placed in patients for treatment. Exemplary punctal plugs include those manufactured by Odyssey Medical (Memphis, Tenn.), and Eagle Vision (Memphis, Tenn.).

In further embodiments, the invention provides methods for treating ear infections, e.g., otitis media, in a subject comprising applying a topical preparation described herein to the ear.

In another embodiment, the invention provides methods for treating demodex mites.

The method described above may further include a rinsing step after a recommended period of exposure. This step preferably comprises a simple water rinse. The topical preparation may be rinsed from the area to which it was applied with ample water after application, e.g., with a hand, finger or any moist pad or cloth suitable for this purpose.

Application of the topical preparations set forth herein can be by any one of a number of art recognized methods. For example, application can be by a applicator, such as a Qtip or pad, by drops from a dropper or bottle, or using a finger or fingers.

One of skill in the art understands that the methods described herein using topical preparations comprising linalool can be also be preformed using compositions comprising α-terpineol oil, and those methods are intended to be included in the scope of this invention.

The topical preparations of the invention may be applied one or more times per day, and may be left in place as long as needed, depending on the intended indication. The number of days which a subject applies the topical preparation, and the duration of the application, will depend on the intent of treatment or on the location and severity infection, and efficacy of the preparations on a given infection. In certain embodiments, the topical preparation may be applied for a period of 30 seconds, 45 seconds, 1 minute, 2 minutes, 3 minutes, 4 minutes, 5 minutes, or longer. The ordinary skilled physician would be able to effectively prescribe a treatment regimen that will be effective in treating or preventing an infection in an individual.

Commercial Applications

The methods and compositions of the invention find numerous commercial applications that could beneficially utilize compliance enhancing methods and compositions for antibacterial applications. Consequently, the invention includes a kit comprising the compositions of the invention, e.g., a kit for the treatment of an ocular disorder, eyelid hygiene, ear infection, of skin infection, in a subject. The kits optionally include an applicator. The topical preparation can be in the form of drops, solution, paste, cream, foam, gel, or ointment, or the like, when included in the kits of the invention.

The kit may optionally be packaged with instructions for use in maintaining eyelid hygiene. The kit may optionally contain a dispenser or applicator, e.g., a sponge, to apply the topical preparations of the invention to the infected area of a subject.

EXAMPLES

It should be appreciated that the invention should not be construed to be limited to the examples that are now described; rather, the invention should be construed to include any and all applications provided herein and all equivalent variations within the skill of the ordinary artisan.

The following experiments were performed with a number of topical preparations to test the efficacy of each preparation against both gram negative and gram positive bacteria. The data is presented in tables showing the organism which the preparation was tested against, the exposure time, the number of survivors, the log reduction and the percent reduction in CFUs (Colony Forming Units).

Experiments were performed with tea tree oil, manuka oil, alpha-terpineol, and linalool in the EyeCI vehicle. The EyeCL vehicle (Advanced Vision Research, Woburn, Mass.) and OcuSoft Lid Scrub Foaming Eyelid Cleanser (CYNACON/OCUSOFT, Rosenberg, Tex.) were tested as controls.

Experiments

Test Substance: EVB-EyeCl-10A 0.25% Tea Tree Oil/0.12% Manuka Oil

| Test Organism | Exposure Time | Test Population Control (CFU/mL) ($Log_{10}$) | Number of Survivors (CFU/mL) ($Log_{10}$) | $Log_{10}$ Reduction | Percent Reduction |
|---|---|---|---|---|---|
| Staphylococcus aureus | 1 minute | $6.4 \times 10^5$ (5.81) | $6.0 \times 10^5$ (5.78) | 0.03 | 6.3% |
| | 5 minutes | | $6.1 \times 10^5$ (5.79) | 0.02 | 4.7% |
| | 30 minutes | | $3.9 \times 10^5$ (5.59) | 0.22 | 39.1% |
| | 1 hours | | $3.4 \times 10^5$ (5.53) | 0.28 | 46.9% |
| | 2 hours | | $2.4 \times 10^5$ (5.38) | 0.43 | 62.5% |
| | 4 hours | | $8.7 \times 10^4$ (4.94) | 0.87 | 86.4% |
| | 8 hours | | $2.0 \times 10^3$ (3.30) | 2.51 | 99.7% |

Test Substance: EVB-EyeCl-10B 0.25% Tea Tree Oil

| Test Organism | Exposure Time | Test Population Control (CFU/mL) ($Log_{10}$) | Number of Survivors (CFU/mL) ($Log_{10}$) | $Log_{10}$ Reduction | Percent Reduction |
|---|---|---|---|---|---|
| Staphylococcus aureus | 1 minute | $6.4 \times 10^5$ (5.81) | $4.7 \times 10^5$ (5.67) | 0.14 | 26.6% |
| | 5 minutes | | $6.8 \times 10^5$ (5.83) | No reduction | No reduction |
| | 30 minutes | | $4.7 \times 10^5$ (5.67) | 0.14 | 26.6% |
| | 1 hours | | $4.6 \times 10^5$ (5.66) | 0.15 | 28.1% |
| | 2 hours | | $4.0 \times 10^5$ (5.60) | 0.21 | 37.5% |
| | 4 hours | | $7.2 \times 10^4$ (4.86) | 0.95 | 88.8% |
| | 8 hours | | $1.7 \times 10^2$ (2.24) | 3.57 | >99.9% |

Test Substance: EVB-EyeCl-10C 0.12% Tea Tree Oil/0.12% Manuka Oil

| Test Organism | Exposure Time | Test Population Control (CFU/mL) ($Log_{10}$) | Number of Survivors (CFU/mL) ($Log_{10}$) | $Log_{10}$ Reduction | Percent Reduction |
|---|---|---|---|---|---|
| Staphylococcus aureus | 1 minute | $6.4 \times 10^5$ (5.81) | $6.6 \times 10^5$ (5.82) | No reduction | No reduction |
| | 5 minutes | | $5.5 \times 10^5$ (5.74) | 0.07 | 14.1% |
| | 30 minutes | | $4.6 \times 10^5$ (5.66) | 0.15 | 28.1% |
| | 1 hours | | $5.2 \times 10^5$ (5.72) | 0.09 | 18.8% |
| | 2 hours | | $3.2 \times 10^5$ (5.51) | 0.30 | 50.0% |
| | 4 hours | | $1.36 \times 10^5$ (5.134) | 0.67 | 78.8% |
| | 8 hours | | $1.20 \times 10^4$ (4.080) | 1.73 | 98.1% |

Test Substance: EVB-EyeCl-10D 2.0% Tea Tree Oil

| Test Organism | Exposure Time | Test Population Control (CFU/mL) ($Log_{10}$) | Number of Survivors (CFU/mL) ($Log_{10}$) | $Log_{10}$ Reduction | Percent Reduction |
|---|---|---|---|---|---|
| Staphylococcus aureus | 1 minute | $6.4 \times 10^5$ (5.81) | $3.5 \times 10^5$ (5.54) | 0.27 | 45.3% |
| | 5 minutes | | $4.6 \times 10^5$ (5.66) | 0.15 | 28.1% |
| | 30 minutes | | $8.9 \times 10^4$ (4.95) | 0.86 | 86.1% |
| | 1 hours | | $5.2 \times 10^4$ (4.72) | 1.09 | 91.9% |
| | 2 hours | | $6.8 \times 10^3$ (3.83) | 1.98 | 98.9% |
| | 4 hours | | $1.4 \times 10^3$ (3.15) | 2.66 | 99.8% |
| | 8 hours | | <2 (<0.3) | >2.2 | >99.999% |

Test Substance: SteriLid (0.25HT) EyeCL Vehicle

| Test Organism | Exposure Time | Test Population Control (CFU/mL) ($Log_{10}$) | Number of Survivors (CFU/mL) ($Log_{10}$) | $Log_{10}$ Reduction | Percent Reduction |
|---|---|---|---|---|---|
| Staphylococcus aureus | 1 minute | $6.4 \times 10^5$ (5.81) | $6.4 \times 10^5$ (5.81) | No reduction | No reduction |
| | 5 minutes | | $6.9 \times 10^5$ (5.83) | No reduction | No reduction |
| | 30 minutes | | $5.9 \times 10^5$ (5.77) | 0.04 | 7.8% |
| | 1 hours | | $5.3 \times 10^5$ (5.72) | 0.09 | 82.8% |
| | 2 hours | | $5.2 \times 10^5$ (5.72) | 0.09 | 82.8% |
| | 4 hours | | $3.9 \times 10^5$ (5.59) | 0.22 | 39.1% |
| | 8 hours | | $8.6 \times 10^5$ (5.93) | No reduction | No reduction |

Test Substance: OcuSoft Lid Scrub Foaming Eyelid Cleanser

| Test Organism | Exposure Time | Test Population Control (CFU/mL) ($Log_{10}$) | Number of Survivors (CFU/mL) ($Log_{10}$) | $Log_{10}$ Reduction | Percent Reduction |
|---|---|---|---|---|---|
| Staphylococcus aureus | 1 minute | $6.4 \times 10^5$ (5.81) | $7.8 \times 10^5$ (5.89) | No reduction | No reduction |
| | 5 minutes | | $5.2 \times 10^5$ (5.72) | 0.09 | 18.8% |
| | 30 minutes | | $7.0 \times 10^5$ (5.85) | No reduction | No reduction |
| | 1 hours | | $3.2 \times 10^5$ (5.51) | 0.30 | 50.0% |
| | 2 hours | | $3.9 \times 10^5$ (5.59) | 0.22 | 39% |
| | 4 hours | | $4.0 \times 10^5$ (5.60) | 0.21 | 38% |
| | 8 hours | | $4.4 \times 10^5$ (5.64) | 0.17 | 31% |

Test Substance: EVB-EyeCl-10A 0.25% Tea Tree Oil/0.12% Manuka Oil

| Test Organism | Exposure Time | Test Population Control (CFU/mL) ($Log_{10}$) | Number of Survivors (CFU/mL) ($Log_{10}$) | $Log_{10}$ Reduction | Percent Reduction |
|---|---|---|---|---|---|
| Pseudomonas aeruginosa | 1 minute | $5.3 \times 10^5$ (5.72) | $1.27 \times 10^5$ (5.104) | 0.62 | 76.0% |
| | 5 minutes | | $3.9 \times 10^4$ (4.59) | 1.13 | 92.6% |
| | 30 minutes | | $1 \times 10^2$ (2.0) | 3.72 | >99.9% |
| | 1 hours | | <2 (<0.3) | >5.4 | >99.999% |
| | 2 hours | | <2 (<0.3) | >5.4 | >99.999% |
| | 4 hours | | <2 (<0.3) | >5.4 | >99.999% |

-continued

Test Substance: EVB-EyeCl-10A 0.25% Tea Tree Oil/0.12% Manuka Oil

| Test Organism | Exposure Time | Test Population Control (CFU/mL) (Log$_{10}$) | Number of Survivors (CFU/mL) (Log$_{10}$) | Log$_{10}$ Reduction | Percent Reduction |
|---|---|---|---|---|---|
| | 8 hours | | <2 (<0.3) | >5.4 | >99.999% |

Test Substance: EVB-EyeCl-10B 0.25% Tea Tree Oil

| Test Organism | Exposure Time | Test Population Control (CFU/mL) (Log$_{10}$) | Number of Survivors (CFU/mL) (Log$_{10}$) | Log$_{10}$ Reduction | Percent Reduction |
|---|---|---|---|---|---|
| Pseudomonas aeruginosa | 1 minute | $5.3 \times 10^5$ (5.72) | $1.49 \times 10^5$ (5.17) | 0.62 | 71.9% |
| | 5 minutes | | $4.0 \times 10^4$ (4.60) | 1.12 | 92.5% |
| | 30 minutes | | 2 (0.3) | 5.4 | >99.999% |
| | 1 hours | | <2 (<0.3) | >5.4 | >99.999% |
| | 2 hours | | <2 (<0.3) | >5.4 | >99.999% |
| | 4 hours | | <2 (<0.3) | >5.4 | >99.999% |
| | 8 hours | | <2 (<0.3) | >5.4 | >99.999% |

Test Substance: EVB-EyeCl-10C 0.12% Tea Tree Oil/0.12% Manuka Oil

| Test Organism | Exposure Time | Test Population Control (CFU/mL) (Log$_{10}$) | Number of Survivors (CFU/mL) | Log$_{10}$ Reduction | Percent Reduction |
|---|---|---|---|---|---|
| Pseudomonas aeruginosa | 1 minute | $5.3 \times 10^5$ (5.72) | $5.0 \times 10^5$ (5.70) | 0.02 | 5.7% |
| | 5 minutes | | $3.4 \times 10^5$ (5.53) | 0.19 | 35.8% |
| | 30 minutes | | $7.2 \times 10^3$ (3.86) | 1.86 | 98.6% |
| | 1 hours | | $5 \times 10^2$ (2.70) | 3.02 | 99.9% |
| | 2 hours | | $3.9 \times 10^4$ (4.59) | 1.13 | 92.6% |
| | 4 hours | | <2 (<0.3) | >5.4 | >99.999% |
| | 8 hours | | <2 (<0.3) | >5.4 | >99.999% |

Test Substance: EVB-EyeCl-10D 2.0% Tea Tree Oil

| Test Organism | Exposure Time | Test Population Control (CFU/mL) (Log$_{10}$) | Number of Survivors (CFU/mL) (Log$_{10}$) | Log$_{10}$ Reduction | Percent Reduction |
|---|---|---|---|---|---|
| Pseudomonas | 1 minute | $5.3 \times 10^5$ (5.72) | $1.0 \times 10^2$ (2.00) | 3.72 | 99.9% |
| aeruginosa | 5 minutes | | <2 (<0.3) | >5.4 | >99.999% |
| | 30 minutes | | <2 (<0.3) | >5.4 | >99.999% |
| | 1 hours | | <2 (<0.3) | >5.4 | >99.999% |
| | 2 hours | | <2 (<0.3) | >5.4 | >99.999% |
| | 4 hours | | <2 (<0.3) | >5.4 | >99.999% |
| | 8 hours | | <2 (<0.3) | >5.4 | >99.999% |

Test Substance: SteriLid (0.25HT) EyeCL Vehicle

| Test Organism | Exposure Time | Test Population Control (CFU/mL) (Log$_{10}$) | Number of Survivors (CFU/mL) (Log$_{10}$) | Log$_{10}$ Reduction | Percent Reduction |
|---|---|---|---|---|---|
| Pseudomonas aeruginosa | 1 minute | $5.3 \times 10^5$ (5.72) | $8.0 \times 10^5$ (5.90) | No reduction | No reduction |
| | 5 minutes | | $8.0 \times 10^5$ (5.90) | No reduction | No reduction |
| | 30 minutes | | $8.6 \times 10^5$ (5.93) | No reduction | No reduction |
| | 1 hours | | $7.9 \times 10^5$ (5.90) | No reduction | No reduction |
| | 2 hours | | $4.6 \times 10^5$ (5.66) | 0.06 | 13.2% |
| | 4 hours | | $1.23 \times 10^5$ (5.090) | 0.63 | 76.8% |
| | 8 hours | | $3.2 \times 10^4$ (4.51) | 1.21 | 94% |

Test Substance: OcuSoft Lid Scrub Foaming Eyelid Cleanser

| Test Organism | Exposure Time | Test Population Control (CFU/mL) (Log$_{10}$) | Number of Survivors (CFU/mL) (Log$_{10}$) | Log$_{10}$ Reduction | Percent Reduction |
|---|---|---|---|---|---|
| Pseudomonas aeruginosa | 1 minute | $5.3 \times 10^5$ (5.72) | $3.2 \times 10^5$ (5.51) | 0.21 | 39.6% |
| | 5 minutes | | $8.0 \times 10^4$ (4.90) | 0.82 | 84.9% |
| | 30 minutes | | $1.01 \times 10^4$ (4.004) | 1.72 | 98.1% |
| | 1 hours | | $3.9 \times 10^3$ (3.59) | 2.13 | 99.3% |
| | 2 hours | | $2.92 \times 10^2$ (2.465) | 3.26 | 99.9% |
| | 4 hours | | 6 (0.8) | 4.92 | >99.99% |
| | 8 hours | | <2 (<0.3) | >5.4 | >99.999% |

This series of experiments indicates that with regard to *S. aureus* killing, tea tree oil alone, in a concentration as high as 2.0% does not achieve a 1 log reduction in colony forming units (CFU). In addition, the data shows that manuka oil does not provide an improvement in *S. aureus* killing. The data also indicate that the EyeCL vehicle (SteriLid (0.25HT) and the product OcuSoft Lid Scrub Foam are not bactericidal. In regard to *Pseudomonas* killing the data indicates that only the 2.0% tea tree oil formulation achieves greater than a 1 log reduction in CFU at one minute.

Test Substance: EyeCl-12A 0.35% Tea Tree Oil/1.5% Linolool

| Test Organism | Exposure Time | Test Population Control (CFU/mL) ($Log_{10}$) | Number of Survivors (CFU/ML) | $Log_{10}$ Reduction | Percent Reduction |
|---|---|---|---|---|---|
| Staphylococcus aureus | 1 minute | $4.1 \times 10^6$ (6.61) | $1.00 \times 10^5$ | 1.61 | 97.6% |
| | 5 minutes | | $3.1 \times 10^4$ | 2.12 | 99.2% |
| | 15 minutes | | $9.4 \times 10^3$ | 2.64 | 99.8% |
| | 30 minutes | | $3.1 \times 10^3$ | 3.12 | 99.9% |

Test Substance: EyeCl-11B 0.5% Tea Tree Oil/0.75% Linalool

| Test Organism | Exposure Time | Test Population Control (CFU/mL) ($Log_{10}$) | Number of Survivors (CFU/mL) | $Log_{10}$ Reduction | Percent Reduction |
|---|---|---|---|---|---|
| Staphylococcus aureus | 1 minute | $4.1 \times 10^6$ (6.61) | $1.62 \times 10^5$ | 1.40 | 96.0% |
| | 5 minutes | | $5.3 \times 10^4$ | 1.89 | 98.7% |
| | 15 minutes | | $3.4 \times 10^4$ | 2.08 | 99.2% |
| | 30 minutes | | $8.7 \times 10^3$ | 2.67 | 99.8% |

Test Substance: EyeCl-12C 1.00% Tea Tree Oil/0.75% Linalool

| Test Organism | Exposure Time | Test Population Control (CFU/mL) ($Log_{10}$) | Number of Survivors (CFU/mL) | $Log_{10}$ Reduction | Percent Reduction |
|---|---|---|---|---|---|
| Staphylococcus aureus | 1 minute | $4.1 \times 10^6$ (6.61) | $3.0 \times 10^5$ | 1.13 | 92.7% |
| | 5 minutes | | $7.9 \times 10^4$ | 1.71 | 98.1% |
| | 15 minutes | | $3.6 \times 10^4$ | 2.05 | 99.1% |
| | 30 minutes | | $8.9 \times 10^3$ | 2.66 | 99.8% |

Test Substance: EyeCl-11D 0.5% Tea Tree Oil/0.75% alpha-terpineol

| Test Organism | Exposure Time | Test Population Control (CFU/mL) ($Log_{10}$) | Number of Survivors (CFU/mL) | $Log_{10}$ Reduction | Percent Reduction |
|---|---|---|---|---|---|
| Staphylococcus aureus | 1 minute | $4.1 \times 10^6$ (6.61) | $7.5 \times 10^4$ | 1.73 | 98.2% |
| | 5 minutes | | $3.1 \times 10^4$ | 2.12 | 99.2% |
| | 15 minutes | | $7.6 \times 10^3$ | 2.73 | 99.8% |
| | 30 minutes | | $3.4 \times 10^3$ | 3.08 | 99.9% |

Test Substance: EyeC-12A 0.35% Tea Tree Oil/1.5% Linolool

| Test Organism | Exposure Time | Test Population Control (CFU/mL) ($Log_{10}$) | Number of Survivors (CFU/mL) | $Log_{10}$ Reduction | Percent Reduction |
|---|---|---|---|---|---|
| Pseudomonas aeruginosa | 1 minute | $1.65 \times 10^7$ (7.217) | <2 | >6.9 | >99.9999% |
| | 5 minutes | | <2 | >6.9 | >99.9999% |
| | 15 minutes | | <2 | >6.9 | >99.9999% |
| | 30 minutes | | <2 | >6.9 | >99.9999% |

Test Substance: EyeCl-11B 0.5% Tea Tree Oil/0.75% Linalool

| Test Organism | Exposure Time | Test Population Control (CFU/mL) ($Log_{10}$) | Number of Survivors (CFU/mL) | $Log_{10}$ Reduction | Percent Reduction |
|---|---|---|---|---|---|
| Pseudomonas aeruginosa | 1 minute | $1.65 \times 10^7$ (7.217) | <2 | >6.9 | >99.9999% |
| | 5 minutes | | <2 | >6.9 | >99.9999% |
| | 15 minutes | | <2 | >6.9 | >99.9999% |
| | 30 minutes | | <2 | >6.9 | >99.9999% |

Test Substance: EyeCl-12C 1.00% Tea Tree Oil/0.75% Linalool

| Test Organism | Exposure Time | Test Population Control (CFU/mL) ($Log_{10}$) | Number of Survivors (CFU/mL) | $Log_{10}$ Reduction | Percent Reduction |
|---|---|---|---|---|---|
| Pseudomonas aeruginosa | 1 minute | $1.65 \times 10^7$ (7.217) | <2 | >6.9 | >99.9999% |
| | 5 minutes | | <2 | >6.9 | >99.9999% |
| | 15 minutes | | <2 | >6.9 | >99.9999% |
| | 30 minutes | | <2 | >6.9 | >99.9999% |

Test Substance: EyeCl-11D 0.5% Tea Tree Oil/0.75% alpha-terpineol

| Test Organism | Exposure Time | Test Population Control (CFU/mL) ($Log_{10}$) | Number of Survivors (CFU/mL) | $Log_{10}$ Reduction | Percent Reduction |
|---|---|---|---|---|---|
| Pseudomonas aeruginosa | 1 minute | $1.65 \times 10^7$ (7.217) | <2 | >6.9 | >99.9999% |
| | 5 minutes | | <2 | >6.9 | >99.9999% |
| | 15 minutes | | <2 | >6.9 | >99.9999% |
| | 30 minutes | | <2 | >6.9 | >99.9999% |

These experiments demonstrate that linalool in concentrations between 0.75% and 1.5%, when combined with tea tree oil concentrations between 0.35% and 1.0%, achieved at least a one log kill of *S. aureus* at 1 minute. Alpha-terpineol at a concentration of 0.75% had a bactericidal effect on *S. aureus* similar to linalool. We note from the prior series of experiments that the tea tree oil was not bactericidal for *S. aureus*. In regard to the effect of these formulations on *P. aeruginosa*, linalool and alpha-terpineol were effective in the concentrations tested in exceeding 1 log reduction in CFU at one minute.

Test Substance: EyeCl-13a (EyeCl-13c diluted 1:1 with water) 0.75% Linalool

| Test Organism | Exposure Time | Test Population Control (CFU/mL) ($Log_{10}$) | Number of Survivors (CFU/mL) | $Log_{10}$ Reduction | Percent Reduction |
|---|---|---|---|---|---|
| Staphylococcus aureus | 30 seconds | $1.02 \times 10^6$ (6.009) | $1.95 \times 10^5$ | 0.719 | 80.9% |
| | 1 minute | | $1.12 \times 10^5$ | 0.960 | 89.0% |
| | 5 minutes | | $7.1 \times 10^4$ | 1.16 | 93.0% |
| | 15 minutes | | $3.7 \times 10^4$ | 1.44 | 96.4% |
| Pseudomonas aeruginosa | 30 seconds | $1.29 \times 10^6$ 6.111 | 8 | 5.2 | 99.999% |
| | 1 minute | | <2 | >5.8 | >99.999% |
| | 5 minutes | | <2 | >5.8 | >99.999% |
| | 15 minutes | | 4 | 5.5 | >99.999% |

Test Substance: EyeCl-13b (EyeCL-13d diluted 1:1 with water) 0.05% Tea Tree Oil .65% Linalool

| Test Organism | Exposure Time | Test Population Control (CFU/mL) ($Log_{10}$) | Number of Survivors (CFU/mL) | $Log_{10}$ Reduction | Percent Reduction |
|---|---|---|---|---|---|
| Staphylococcus aureus | 30 seconds | $1.02 \times 10^6$ (6.009) | $1.28 \times 10^5$ | 0.902 | 87.5% |
| | 1 minute | | $1.21 \times 10^5$ | 0.926 | 88.1% |
| | 5 minutes | | $6.4 \times 10^4$ | 1.20 | 93.7% |
| | 15 minutes | | $3.5 \times 10^4$ | 1.47 | 96.6% |
| Pseudomonas aeruginosa | 30 seconds | $1.29 \times 10^6$ 6.111 | $1.4 \times 10^1$ | 4.96 | 99.99% |
| | 1 minute | | <2 | >5.8 | >99.999% |
| | 5 minutes | | <2 | >5.8 | >99.999% |
| | 15 minutes | | <2 | >5.8 | >99.999% |

Test Substance: Eye-Cl-13c 1.5% Linalool

| Test Organism | Exposure Time | Test Population Control (CFU/mL) ($Log_{10}$) | Number of Survivors (CFU/mL) | $Log_{10}$ Reduction | Percent Reduction |
|---|---|---|---|---|---|
| Staphylococcus aureus | 30 seconds | $1.02 \times 10^6$ (6.009) | $9.9 \times 10^4$ | 1.02 | 90.3% |
| | 1 minute | | $5.2 \times 10^4$ | 1.29 | 94.9% |
| | 5 minutes | | $5.3 \times 10^4$ | 1.29 | 94.8% |
| | 15 minutes | | $1.38 \times 10^4$ | 1.869 | 98.6% |
| Pseudomonas aeruginosa | 30 seconds | $1.29 \times 10^6$ 6.111 | <2 | >5.8 | >99.999% |
| | 1 minute | | <2 | >5.8 | >99.999% |
| | 5 minutes | | <2 | >5.8 | >99.999% |
| | 15 minutes | | <2 | >5.8 | >99.999% |

Test Substance: EyeCl-13D 0.10% Tea Tree Oil and 1.25% Linalool

| Test Organism | Exposure Time | Test Population Control (CFU/mL) ($Log_{10}$) | Number of Survivors (CFU/mL) | $Log_{10}$ Reduction | Percent Reduction |
|---|---|---|---|---|---|
| Staphylococcus aureus | 30 seconds | $1.02 \times 10^6$ (6.009) | $8.4 \times 10^4$ | 1.09 | 91.8% |
| | 1 minute | | $6.3 \times 10^4$ | 1.21 | 93.8% |
| | 5 minutes | | $1.52 \times 10^4$ | 1.826 | 98.5% |
| | 15 minutes | | $1.33 \times 10^4$ | 1.956 | 98.7% |
| Pseudomonas | 30 seconds | $1.29 \times 10^6$ 6.111 | 4 | 5.5 | 99.999% |
| | 1 minute | | 4 | 5.5 | 99.999% |
| aeruginosa | 5 minutes | | <2 | >5.8 | >99.999% |
| | 15 minutes | | <2 | >5.8 | >99.999% |

This experiment shows that 0.75% linalool alone virtually achieves 1 log reduction in *S. aureus* and *P. aeruginosa* killing at 1 minute. Formulations 13b and 13d continue to be consistent with a lack of *S. aureus* killing with tea tree oil. Linalool 0.75% alone was sufficient to achieve greater than 1 log of *Pseudomonas* killing at 1 one minute.

Test Substance: (EyeCl-15a) 0.85 Linalool/0.025% TTO

| Test Organism | Exposure Time | Test Population Control (CFU/mL) ($Log_{10}$) | Number of Survivors (CFU/ML) | $Log_{10}$ Reduction | Percent Reduction |
|---|---|---|---|---|---|
| Staphylococcus aureus | 30 seconds | $3.3 \times 10^6$ (6.52) | $3.5 \times 10^5$ | 0.98 | 89.4% |
| | 1 minute | | $2.25 \times 10^5$ | 1.17 | 93.2% |
| | 5 minutes | | $2.07 \times 10^5$ | 1.20 | 93.7% |
| | 15 minutes | | $1.61 \times 10^5$ | 1.31 | 95.1% |

In this experiment 0.85% linalool achieves greater than a 1 log reduction in *S. aureus* at 1 minute. Tea tree oil was included in the formulation for its anti-inflammatory properties.

In the following set of experiments, a composition comprising 0.025% Tea Tree Oil and 0.85% Linalool was tested against a number of gram positive and gram negative bacteria.

Test Substance: EyeCl-15A 0.025% Tea Tree Oil and 0.85% Linalool

| Test Organism | Exposure Time | Test Population Control (CFU/mL) ($Log_{10}$) | Number of Survivors (CFU/mL) | $Log_{10}$ Reduction | Percent Reduction |
|---|---|---|---|---|---|
| Pseudomonas aeruginosa | 30 seconds | $1.84 \times 10^7$ (7.265) | $1.5 \times 10^2$ | 5.09 | >99.999% |
| | 1 minute | | $4.6 \times 10^1$ | 5.61 | >99.999% |
| | 5 minutes | | 6 | 6.5 | >99.9999% |
| | 15 minutes | | 6 | 6.5 | >99.9999% |
| Moraxella (Branhamella) catarrhalis | 30 seconds | $1.29 \times 10^7$ (7.111) | <2 | >6.8 | >99.999% |
| | 1 minute | | <2 | >6.8 | 99.999% |
| | 5 minutes | | <2 | >6.8 | >99.999% |
| | 15 minutes | | <2 | >6.8 | >99.999% |
| Escherichia Coli | 30 seconds | $2.17 \times 10^7$ (7.336) | <2 | >7 | >99.99999% |
| | 1 minute | | <2 | >7 | 99.99999% |
| | 5 minutes | | <2 | >7 | >99.99999% |
| | 15 minutes | | <2 | >7 | >99.99999% |
| Serratia marcescens | 30 seconds | $1.17 \times 10^7$ (7.068) | $3.0 \times 10^3$ | 3.59 | >99.9% |
| | 1 minute | | $3.16 \times 10^2$ | 4.568 | 99.99% |
| | 5 minutes | | $8.2 \times 10^1$ | 5.16 | >99.999% |
| | 15 minutes | | $5.6 \times 10^1$ | 5.32 | >99.999% |

Test Substance: EyeCl-15A 0.025% Tea Tree Oil and 0.85% Linalool

| Test Organism | Exposure Time | Test Population Control (CFU/mL) ($Log_{10}$) | Number of Survivors (CFU/mL) | $Log_{10}$ Reduction | Percent Reduction |
|---|---|---|---|---|---|
| Staphylo- | 30 seconds | $9.0 \times 10^5$ | $1.46 \times 10^5$ | 0.79 | 83.8% |
| coccus | 1 minute | (5.95) | $1.29 \times 10^5$ | 0.84 | 85.7% |
| aureus | 5 minutes | | $8.1 \times 10^4$ | 1.04 | 91.0% |
| | 15 minutes | | $4.2 \times 10^4$ | 1.33 | 95.3% |
| Staphylo- | 30 seconds | $3.9 \times 10^6$ | $7.1 \times 10^4$ | 1.74 | 98.2% |
| coccus | 1 minute | (6.59) | $8.9 \times 10^3$ | 2.65 | 99.8% |
| aureus- | 5 minutes | | $1.0 \times 10^2$ | 4.59 | 99.99% |
| MRSA | 15 minutes | | $2.0 \times 10^1$ | 5.29 | 99.999% |
| Staphylo- | 30 seconds | $1.22 \times 10^6$ | $9.8 \times 10^5$ | 0.10 | 19.7% |
| coccus | 1 minute | (6.086) | $9.4 \times 10^5$ | 0.12 | 23.0% |
| warneri | 5 minutes | | $6.9 \times 10^5$ | 0.25 | 43.4% |
| | 15 minutes | | $4.5 \times 10^5$ | 0.44 | 63.1% |
| Staphylo- | 30 seconds | $9.2 \times 10^5$ | $1.76 \times 10^4$ | 1.71 | 98.1% |
| coccus | 1 minute | (5.96) | $6.2 \times 10^3$ | 2.17 | 99.3% |
| epider- | 5 minutes | | $4.88 \times 10^2$ | 3.27 | 99.9% |
| midis | 15 minutes | | $9.6 \times 10^{1\,4}$ | 3.98 | 99.9% |

The preceding examples demonstrate that a number of the topical preparations tested were effective against both gram negative and gram positive bacteria. Moreover, the data indicate that these compositions were also effective against antibiotic resistant bacterial strains.

The following table sets forth an exemplary topical preparation of the invention.

EyeCL-16a Formula

| Raw Materials | % By Weight |
|---|---|
| Tri SODIUM EDTA | 0.03 |
| ALLANTOIN | 0.10 |
| BORIC ACID | 0.20 |
| PANTHENOL | 0.10 |
| SODIUM CHLORIDE | 0.85 |
| SODIUM PERBORATE | 0.03 |
| TURPINAL | 0.01 |
| COLADET BSB | 5.00 |
| COLALIPID C | 0.05 |
| HEPES ACETATE | 0.25 |
| TEA TREE OIL | 0.03 |
| LINALOOL | 0.90 |
| CIRTIC ACID 40% SOL'N | As necessary |
| PURIFIED WATER | 92.51 |

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of cleaning skin of a subject in need thereof consisting essentially of topically applying an aqueous gel or foam composition to the skin of said subject consisting essentially of 0.7 wt. % to about 1.5 wt. % linalool, 0.0125 wt. % to about 0.050 wt % tea tree oil and a chelator selected from the group consisting of EDTA, nitrilotriacetate, sodium hexametaphosphate, acetylsalicylate and ascorbate and wherein the aqueous gel or foam composition is bacteriostatic or bactericidal against gram negative bacteria and gram positive bacteria.

2. The method of claim 1, wherein the linalool is present in a concentration of between about 0.80% and about 1.25% by weight.

3. The method of claim 1, wherein the concentration of the linalool is about 0.90% by weight.

4. The method of claim 1, wherein the tea tree oil is present in a concentration of between about 0.02% to about 0.04% by weight.

5. The method of claim 1, wherein the concentration of the tree tea oil is about 0.025% by weight.

6. The method of claim 1, wherein the membrane permeablizer is trisodium EDTA.

7. The method of claim 1 wherein the membrane permeablizer is trisodium EDTA and the concentration of the trisodium EDTA is about 0.03% by weight.

8. The method of claim 1 wherein the aqueous gel or foam composition is topically applied to the eyelid.

9. The method of claim 8 wherein the aqueous gel or foam composition membrane has about 0.03% by weight trisodium EDTA.

10. The method of claim 8, wherein the linalool is present in a concentration of between about 0.80% and about 1.25% by weight.

11. The method of claim 8, wherein the concentration of the linalool is about 0.90% by weight.

12. The method of claim 8, wherein the tea tree oil is present in a concentration of between about 0.02% to about 0.04% by weight.

13. The method of claim 8, wherein the concentration of the tree tea oil is about 0.025% by weight.

* * * * *